US012715838B2

(12) United States Patent
Haaland et al.

(10) Patent No.: US 12,715,838 B2
(45) Date of Patent: Aug. 25, 2026

(54) CONTINUOUS CRYSTALLISATION METHOD

(71) Applicant: GE Healthcare AS, Oslo (NO)

(72) Inventors: Torfinn Haaland, Lindesnes (NO); Arne Askildsen, Lindesnes (NO); Heidi Kvande, Lindesnes (NO)

(73) Assignee: GE Healthcare AS, Oslo (NO)

( * ) Notice: Subject to any disclaimer, the term of this patent is extended or adjusted under 35 U.S.C. 154(b) by 882 days.

(21) Appl. No.: 17/912,646

(22) PCT Filed: Mar. 31, 2021

(86) PCT No.: PCT/EP2021/058529
§ 371 (c)(1),
(2) Date: Sep. 19, 2022

(87) PCT Pub. No.: WO2021/198386
PCT Pub. Date: Oct. 7, 2021

(65) Prior Publication Data

US 2023/0133715 A1 May 4, 2023

(30) Foreign Application Priority Data

Mar. 31, 2020 (GB) ..................................... 2004773

(51) Int. Cl.
*C07C 231/24* (2006.01)
*C07C 237/46* (2006.01)

(52) U.S. Cl.
CPC .......... *C07C 231/24* (2013.01); *C07C 237/46* (2013.01)

(58) Field of Classification Search
None
See application file for complete search history.

(56) References Cited

U.S. PATENT DOCUMENTS 7,754,920 B1 * 7/2010 Holmaas ............... C07C 231/24 564/219
8,163,965 B2 * 4/2012 Cervenka ............. C07C 17/392 570/190

(Continued)

FOREIGN PATENT DOCUMENTS

CN 101248027 A 8/2008
CN 101962340 A 2/2011

(Continued)

OTHER PUBLICATIONS

Alvarez ("Continuous Plug Flow Crystallization of Pharmaceutical Compounds" Crystal Growth and Design Article, 2010, p. 2219) (Year: 2010).*

(Continued)

*Primary Examiner* — Amy C Bonaparte

(74) *Attorney, Agent, or Firm* — Lathrop GPM LLP; Malaika O.D. Tyson

(57) ABSTRACT

The invention provides a method of purifying 5-acetamido-N,N'-bis(2,3-dihydroxypropyl)-2,4,6-triiodoisophathalamide, comprising adding a portion of acid to a stream comprising crude 5-acetamido-N,N'-bis(2,3-dihydroxypropyl)-2,4,6-triiodoisophathalamide in a solvent and continuously crystallising the 5-acetamido-N,N'-bis(2,3-dihydroxypropyl)-2,4,6-triiodoisophathalamide from the crude 5-acetamido-N,N'-bis(2,3-dihydroxypropyl)-2,4,6-triiodoisophathalamide, with removal of at least a fraction of the (Continued)

solvent, wherein the crystallisation is carried out in a continuous reactor, wherein the continuous reactor is a plug flow reactor. At least three further portions of acid are added to the continuous reactor during the crystallisation.

14 Claims, 1 Drawing Sheet

(56) References Cited

U.S. PATENT DOCUMENTS

| | | | | |
|---|---|---|---|---|
| 9,688,614 | B2 * | 6/2017 | Saanum | C07C 231/02 |
| 2011/0021822 | A1 * | 1/2011 | Askildsen | C07C 237/46 |
| | | | | 564/153 |
| 2016/0304438 | A1 | 10/2016 | Saanum et al. | |

FOREIGN PATENT DOCUMENTS

| | | | |
|---|---|---|---|
| CN | 105764882 | A | 7/2016 |
| CN | 105793235 | A | 7/2016 |
| CN | 105873898 | A | 8/2016 |
| EP | 2281791 | A1 | 2/2011 |
| JP | 2020-037054 | A | 3/2020 |
| WO | 2007013816 | A1 | 2/2007 |
| WO | 2015082720 | A1 | 6/2015 |
| WO | 2016193740 | A1 | 12/2016 |

OTHER PUBLICATIONS

Wood ("Progress to Date in the Design and Operation of Continuous Crystallization Processes for Pharmaceutical Applications" Org. Process. Res. Dev. 2019, p. 122) (Year: 2019).*

SciFinder Entry for RN 31127-80-7, downloaded on Aug. 14, 2025. (Year: 2025).*

Chinese Patent Office, "Office Action," regarding Application No. 202180025772.9, 14 pages with translation, dated Nov. 23, 2023.

Search Report received in German Application No. 2004773.4 dated Sep. 18, 2020, 4 pages.

Search Report received in International Application No. PCT/EP2021/058529 dated Jun. 24, 2021, with translation, 4 pages.

Written Opinion received in International Application No. PCT/EP2021/058529 dated Jun. 24, 2021, 7 pages.

Japanese Office Action for Japanese Patent Application No. 2022-559762, mailed Apr. 15, 2025.

Mcglone et al., "Oscillatory Flow Reactors (OFRs) for Continuous Manufacturing and Crystallization", Organic Process Res. & Dev., Aug. 6, 2015, 19(9): 1186-1202.

Korean Office Action for Korean Patent Application No. 10-2022-7033340 mailed Nov. 7, 2025, 14 pages.

* cited by examiner

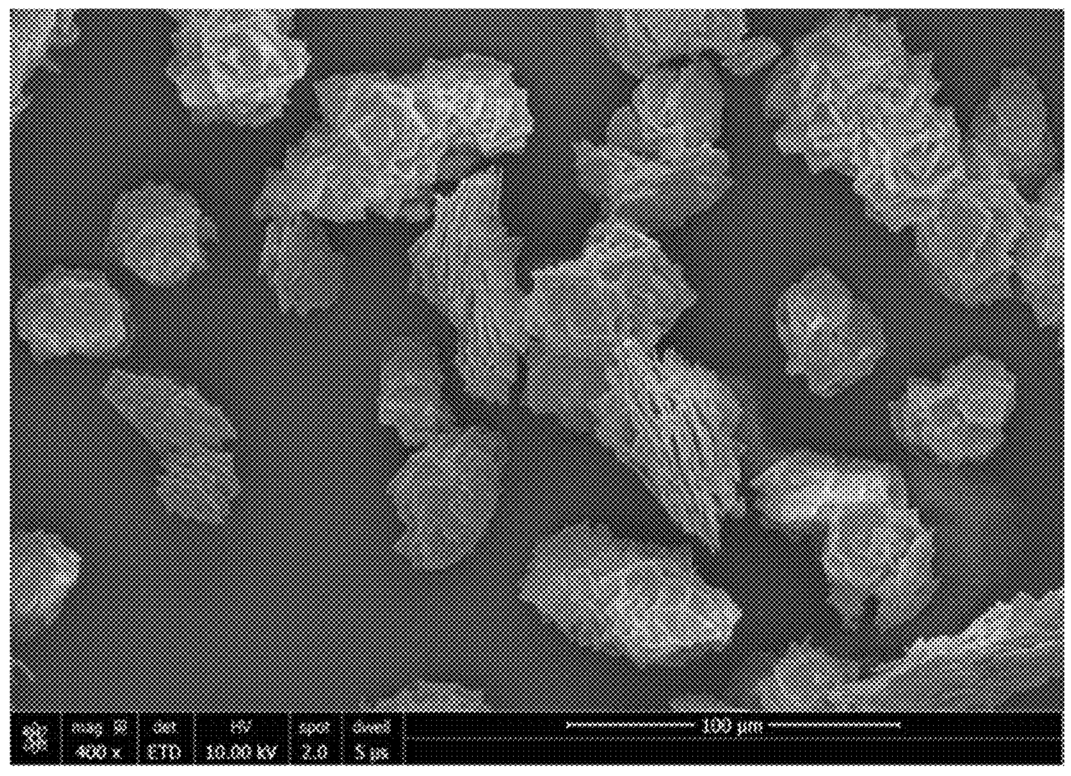
mag
400 x
det
ETD
HV
10.00 kV
spot
2.0
dwell
5 µs
100 µm
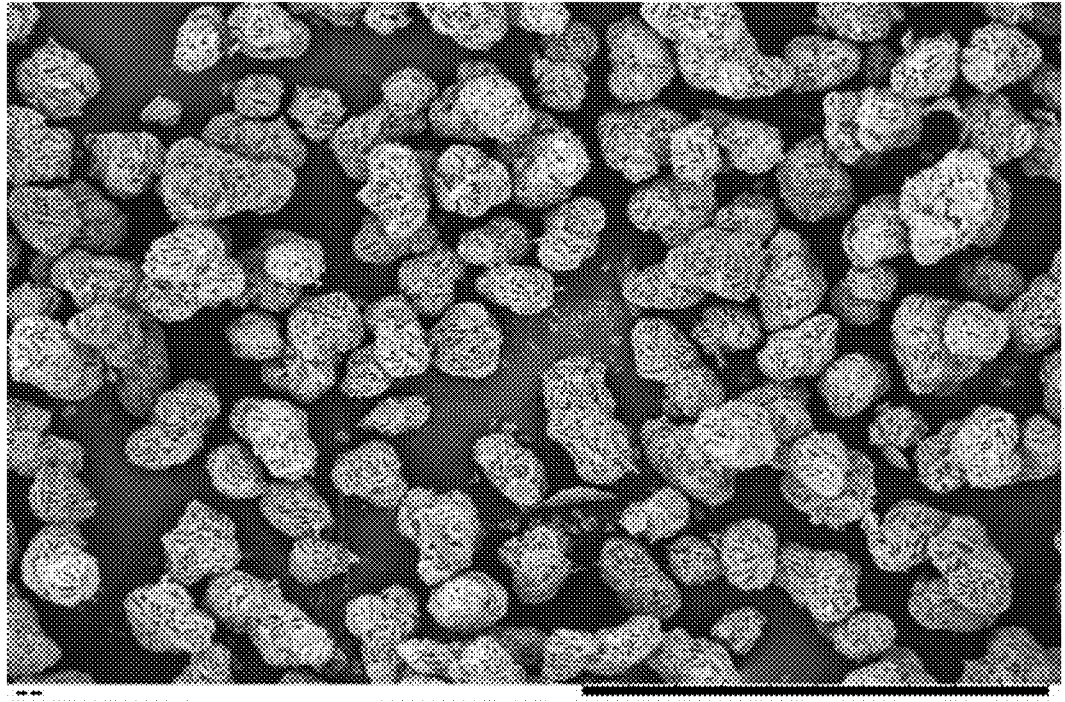
TM3030Plus
2017/03/08
15:41 HL MD8.1
x150
500 µm

CONTINUOUS CRYSTALLISATION METHOD

The present invention relates to a method of purifying 5-acetamido-N,N'-bis(2,3-dihydroxypropyl)-2,4,6-triiodo-isophathalamide and to the 5-acetamido-N,N'-bis(2,3-dihydroxypropyl)-2,4,6-triiodoisophathalamide (hereafter the 'compound of the invention') produced by such a process.

The present invention provides advantages over prior art processes for purifying this compound.

The prior art purifies 5-acetamido-N,N'-bis(2,3-dihydroxypropyl)-2,4,6-triiodoisophathalamide by batch reactor. Methods in the prior art include adding hydrochloric acid to a reaction mixture until it is turning turbid, adding seed for the compound to be purified, stirring the resulting slurry before additional hydrochloric acid is added. The slurry is then cooled (e.g. to approximately 20-25° C.) overnight. The following day, the slurry is filtered and the filter cake washed with methanol and then dried in a vacuum oven. Such a process is described in US 2016/304438.

Improvements in the purification of commercially useful compounds (such as the compound of the invention) on an industrial scale is a continuous aim.

The present invention relates to a method of purifying 5-acetamido-N,N'-bis(2,3-dihydroxypropyl)-2,4,6-triiodo-isophathalamide, comprising:

(i) adding a portion of acid to a stream comprising crude 5-acetamido-N,N'bis(2,3-dihydroxypropyl)-2,4,6-triiodoisophathalamide in a solvent;

(ii) continuously crystallising 5-acetamido-N,N'-bis(2,3-dihydroxypropyl)-2,4,6-triiodoisophathalamide from the crude 5-acetamido-N,N'-bis(2,3-dihydroxypropyl)-2,4,6-triiodoisophathalamide, with removal of at least a fraction of the solvent, wherein the crystallisation is carried out in a continuous reactor, wherein the continuous reactor is a plug flow reactor;

wherein at least three further portions of acid are added to the continuous reactor during the crystallisation.

The process is thus a continuous reactor process, where the reactor is a plug flow reactor. Also disclosed is the method described here using any kind of continuous reactor. For example, a COBR (continuous oscillation baffle reactor), or a continuous stirred tank reactor (CSTR) may be used with any of the methods described here.

The method of the invention is preferably carried out at a temperature of between 20° C. to 60° C., typically starting at approximately 60° C. followed by cooling to approximately 20° C. If the reaction mixture in which the crude compound of the invention is produced (before purification) is at a higher temperature, then cooling will be required.

The acid used in the method may be a water-soluble inorganic acid and is preferably selected from the group of sulphuric acid, nitric acid and hydrochloric acid. The acid is most preferably hydrochloric acid.

The acid in step (i) of the process may be added to the stream comprising the crude compound of the invention in an amount of 0.3-0.6 molar equivalents, 0.4-0.5 molar equivalents, or 0.45 molar equivalents with respect to the compound of the invention in the crude mixture.

The at least three further portions of acid may each be added to the continuous reactor in an amount of 0.05-0.6 molar equivalents with respect to the compound of the invention in the crude mixture.

The at least three portions of acid may be added to the continuous reactor in an amount of between 0.1 and 0.5 molar equivalents with respect to the compound of the invention in the crude mixture.

More particularly, at least five further portions of acid may be added to the continuous reactor, where:

(i) the first of the at least five further portions of acid may added to the continuous reactor in an amount of 0.1-0.2 molar equivalents with respect to the compound of the invention in the crude mixture;

(ii) the second of the at least five portions of acid may be added to the continuous reactor in an amount of 0.5-1.5 molar equivalents with respect to the compound of the invention in the crude mixture;

(iii) the third of the at least five portions of acid may be added to the continuous reactor in an amount of 0.5-1.5 molar equivalents with respect to the compound of the invention in the crude mixture;

(iv) the fourth of the at least five portions of acid may be added to the continuous reactor in an amount of 0.03-0.11 molar equivalents with respect to the compound of the invention in the crude mixture; and (v) the fifth of the at least five portions of acid may be added to the continuous reactor in an amount of 0.1-0.5 molar equivalents with respect to the compound of the invention in the crude mixture.

In the method of the invention, at least five further portions of acid may be added to the continuous reactor, where:

(i) the first of the at least five further portions of acid may be added at a time between 9% and 19% of the total residence time; and/or (ii) the second of the at least five portions of acid may be added at a time between 31% and 41% of the total residence time; and/or (iii) the third of the at least five portions of acid may be added at a time between 44% and 54% of the total residence time; and/or (iv) the fourth of the at least five portions of acid may be added at a time between 61% and 71% of the total residence time; and/or (v) the fifth of the at least five portions of acid may be added at a time between 84% and 94% of the total residence time.

The at least five further portions of acid may be added to the continuous reactor, where:

(i) the first of the at least five further portions of acid may be added at a time between 13% and 16% of the total residence time; and/or (ii) the second of the at least five portions of acid may be added at a time between 34.5% and 37.5% of the total residence time; and/or (iii) the third of the at least five portions of acid may be added at a time between 48% and 51% of the total residence time; and/or (iv) the fourth of the at least five portions of acid may be added at a time between 66% and 69% of the total residence time; and/or (v) the fifth of the at least five portions of acid may be added at a time between 88% and 91% of the total residence time.

Options (i)-(v) for the above timings may be combined as preferred.

Where at least five further portions of acid are added to the continuous reactor, the continuous reactor may be any kind of continuous reactor. In particular, the continuous reactor may be one of: a plug flow reactor, a COBR (continuous oscillation baffle reactor), or a continuous stirred tank reactor (CSTR). In particular, the acid may be hydrochloric acid.

The purification process time is typically in the region of approximately 40 minutes to 3 hours, optionally 1-2 hours.

The total amount of acid added in steps (i) and (ii) of the method is preferably 1 to 1.4 molar equivalents with respect to the crude compound of the invention being purified, most preferably approximately 1.2 molar equivalents with respect to the crude compound of the invention being purified.

Seed crystals may be added to the continuous reactor in the method. The initial slurry of seed crystal is not a limiting factor. The seed crystals are preferably added to the continuous reactor with or after the first acid portion and before the at least three further portions of acid are added to the continuous reactor.

The first portion of acid is preferably added to the continuous reactor at the inlet of the process stream.

The solvent used in the method may be any solvent for crude compound of the invention. For example, the solvent can include water, methanol, 2-metoxy-ethanol or any mixture. Examples of further suitable solvents include: ethers, such as diethyl ether, tetrahydrofuran, dioxane or dimethoxyethane; alcohols, such as methanol or ethanol; and water. Of these, alcohols, particularly methanol, or a mixture of water and one or more alcohols are preferred.

In the method of the invention, the solvent is preferably removed by: (i) distillation or (ii) azeotropic distillation, which optionally may either be carried out under reduced pressure.

The crystallisation process may be performed in one or more crystallisation units, preferably wherein the crude compound of the invention is fed into the crystallisation units at constant rates. The crystalline compound of the invention is preferably withdrawn at a constant rate, more preferably a rate where the volume load of the crystallisation unit is kept constant.

In accordance with the invention, the acid (at each stage and/or total) may be added until a specific pH is reached. The pH of the total may be approximately pH 2-8, preferably 5-7.

In the invention, the acid in step (i) may be added to the stream comprising a crude compound of the invention until the stream is supersaturated with respect to the crude compound of the invention.

In an embodiment of the method of the invention, each of the second to fourth of the at least five further portions of acid may be added at a time period (interval) which is within 20% of the time period between the previous two acid portion additions. Preferably, each of the time periods between acid portion additions is between 5 and 15 minutes, more preferably between 6 and 12 minutes. The time period between the addition of the first and second of the at least five further acid portions and the fourth and fifth of the acid portions may be similar and within 10% of the time. Preferably, the time period between the third and fourth of the at least five further acid additions are the shortest time period between the addition of any two acid additions.

The invention also provides a purified compound of the invention, produced by the method of the invention.

The purification method of the invention will be preceded in some form by the formation of the compound of the invention itself, which formation process is not required, but can be part of the method of the invention as claimed. In one example method of formation, 5-amino-N,N'-bis(2,3-dihydroxypropyl)-2,4,6-triiodo-1,3-benzenedicarboxamide is mixed with acetic anhydride/acetic acid to form a slurry. The slurry is then heated to approximately 60° C., and an acid catalyst is added to the reaction, maintaining the reaction temperature between 65° C. to 85° C. The last step has a deacetylating agent added, before producing to purification of the product. The acid catalyst may be a sulfonic acid.

The present invention is a continuous crystallization method, which is fundamentally different from a batch crystallization method (in a batch reactor). In the former, the supersaturation at a given point in the reactor is constant over time. In other words, the supersaturation is a function of distance from the reactor inlet. In the latter, supersaturation is function of time. Therefore, it was not expected or anticipated that prior art batch crystallization would be transferable to continuous mode (plug flow reactor) in a competitive way and on an industrial scale. Indeed, various methodologies (outside of the method of this invention) of the process in a continuous process were not suitable. However, due to production capacity needs and current capacity constraints, there was a need to look for alternative processes to purify iodinated aryl compound and the inventors solved problems with the transfer to a continuous process to produce the method of the invention. The present invention was found to have advantages of reduced footprint, lower investment costs, reproducibility, and filtration behavior of crystals.

The crystals obtained using the method of the invention were observed to be a different shape from those obtained using prior methods (see FIG. 1: inventive method top; prior method below). The crystals from the invention were easier to separate from mother liquor, to pre-dry, and to remove salts and by-products. It was also observed that the crystals of the invention were less prone to "scaling", i.e. growth of the crystals on the wall of the reactor that may over time lead to blockage of the reactor. From an industrial point of view, this is advantageous as it means less investment is required to achieve a defined filtration capacity.

The present invention relates to the purification of compound of the invention by reaction crystallization in continuous mode. The method is hence quite specific and therefore not suitable for other, even closely related, iodinated compounds.

In preliminary studies prior to arriving at the present invention, it was explored how the hydrochloric acid could be added for giving crystals that were easy handleable by filtration, washing and drying. For a short and easy crystallization, it was thought to be beneficial to have as few additions of hydrochloric acid as possible. This can generate, however, a higher supersaturation which in turn could lead to formation of crystals that are difficult to handle, and there is also a higher risk for scaling inside the tube walls in a plug-flow reactor. In some experiments, all hydrochloric acid was added in one portion. Such a crystallization was impossible to control due to high supersaturation. In the inventive method hydrochloric acid is added in several portions as described in the examples below.

EXAMPLES

The present invention is described with reference to the following examples. While HCl is used in the following Examples, any water-soluble inorganic acid may be used, as discussed above.

Example 1

The total amount of hydrochloric acid used was 1.2 molar equivalents with respect to the compound of the invention to be purified.

In the first experimental "package", in which 8 experiments were carried out, the amount of hydrochloric acid was divided in four portions. The first portion (0.45 molar equivalents) was added at the inlet at 60° C. The slurry of seed crystals (1.7 w/w % with respect to total amount of the compound crystallized) was added 3.4 minutes after inlet. The second portion of hydrochloric acid (0.15 molar equivalents) was added 6.6 minutes after inlet. The third (0.20 molar equivalents) and fourth (0.40 molar equivalents) portion were added 16.3 minutes and 25.8 minutes after inlet, respectively. The cooling (from 60° C. to 20° C.) started 34.6 minutes after inlet and took 12.4 minutes. Hence the total time for the hydrochloric acid additions was 25.8 minutes whereas the total process time was 47.0 minutes. The COBR reactor was operated with an amplitude of 40 mm and a frequency of 1.5 Hz.

In the following experiments, different combinations of amplitude and frequency were investigated. The concentration (not the amount) of hydrochloric acid was reduced from 17.5% to 8.75% in the fourth portion in some of the experiments.

Two changes were made in the next experiment. First, the frequency was reduced from 1.5 Hz to 1.3 Hz. Second, the concentration (not the amount) of hydrochloric acid was reduced from 17.5% to 8.75% in the fourth portion. The frequency was reduced further from 1.3 Hz to 1.2 Hz and was then increased again. A combination of 1.5 Hz frequency and 30 mm amplitude was also tried Overall, the product quality of the crystals and the filtration behavior were acceptable. Some scaling was observed nearby the third and fourth addition point of hydrochloric acid. However, this would most probably be resolved by going from laboratory scale to industrial scale. In the latter case, the diameter of the pipe would be much larger and hence more of the supersaturation generated by adding hydrochloric acid would be taken out in the fluid rather than by crystallization on the wall.

Example 2

Several experiments were performed in a second "package". The frequency and amplitude were 1.3 Hz and 35 mm, respectively, in all experiments.

The amount of seed slurry was 2.0 w/w % in all experiments. The cooling from 60° C. to 20° C. was performed in a CSTR reactor placed subsequent to the outlet of the COBR reactor. These parameters, as well as the frequency and amplitude were standard and determined not to be critical for the method of the invention. The total amount of hydrochloric acid added in the COBR reactor was 1.0 or 1.2 molar equivalents with respect to the compound being purified. The hydrochloric acid was divided into six portions in all experiments (in contrast to the first "package" where the hydrochloric acid was divided into four portions).

In the first experiment the first portion (0.45 molar equivalents) was added at the inlet. The slurry of seed crystals was added 2.8 minutes after the inlet. The second portion of hydrochloric acid (0.15 molar equivalents) was added 7.6 minutes after the inlet. The third portion (0.10 molar equivalents) was added 19.1 minutes after the inlet, the fourth portion (0.10 molar equivalents) was added 26.2 minutes after the inlet, the fifth portion (0.20 molar equivalents) was added 35.7 minutes after the inlet and the sixth portion (0.20 molar equivalents) was added 43.3 minutes after the inlet. The time at the outlet (from COBR to CSTR) was 52.8 minutes.

Differences from experiment 1 to experiment 2 are bolded below.

In the second experiment the first portion (0.48 molar equivalents) was added at the inlet. The slurry of seed crystals was added 2.8 minutes after the inlet. The second portion of hydrochloric acid (0.18 molar equivalents) was added 7.6 minutes after the inlet. The third portion (0.10 molar equivalents) was added 19.1 minutes after the inlet, the fourth portion (0.10 molar equivalents) was added 26.2 minutes after the inlet, the fifth portion (0.11 molar equivalents) was added 35.7 minutes after the inlet and the sixth portion (0.23 molar equivalents) was added 43.3 minutes after the inlet. The time at the outlet (from COBR to CSTR) was 52.8 minutes.

Differences from experiment 2 to experiment 3 are bolded below.

In the third experiment the first portion (0.45 molar equivalents) was added at the inlet. The slurry of seed crystals was added 2.8 minutes after the inlet. The second portion of hydrochloric acid (0.15 molar equivalents) was added 7.6 minutes after the inlet. The third portion (0.10 molar equivalents) was added 19.1 minutes after the inlet, the fourth portion (0.10 molar equivalents) was added 26.2 minutes after the inlet, the fifth portion (0.10 molar equivalents) was added 35.7 minutes after the inlet and the sixth portion (0.10 molar equivalents) was added 43.3 minutes after the inlet. Please note that the total amount of hydrochloric acid was 1.0 molar equivalents (instead of 1.2). The time at the outlet (from COBR to CSTR) was 52.8 minutes.

Differences from experiment 3 to experiment 4 are bolded below.

In the fourth experiment the first portion (0.45 molar equivalents) was added at the inlet. The slurry of seed crystals was added 2.8 minutes after the inlet. The second portion of hydrochloric acid (0.15 molar equivalents) was added 7.6 minutes after the inlet. The third portion (0.10 molar equivalents) was added 19.1 minutes after the inlet, the fourth portion (0.10 molar equivalents) was added 26.2 minutes after the inlet, the fifth portion (0.08 molar equivalents) was added 35.7 minutes after the inlet and the sixth portion (0.12 molar equivalents) was added 43.3 minutes after the inlet. Please note that the total amount of hydrochloric acid was 1.0 molar equivalents (instead of 1.2). The time at the outlet (from COBR to CSTR) was 52.8 minutes.

Differences from experiment 4 to experiment 5 are bolded below.

In the fifth experiment the first portion (0.45 molar equivalents) was added at the inlet. The slurry of seed crystals was added 2.8 minutes after the inlet. The second portion of hydrochloric acid (0.15 molar equivalents) was added 7.6 minutes after the inlet. The third portion (0.10 molar equivalents) was added 19.1 minutes after the inlet, the fourth portion (0.10 molar equivalents) was added 26.2 minutes after the inlet, the fifth portion (0.08 molar equivalents) was added 35.7 minutes after the inlet and the sixth portion (0.16 molar equivalents) was added 43.3 minutes after the inlet. Please note that the total amount of hydrochloric acid was 1.04 molar equivalents (instead of 1.2). The time at the outlet (from COBR to CSTR) was 52.8 minutes.

Differences from experiment 5 to experiment 6 are bolded below.

In the sixth experiment the first portion (0.45 molar equivalents) was added at the inlet. The slurry of seed crystals was added 2.8 minutes after the inlet. The second portion of hydrochloric acid (0.15 molar equivalents) was added 7.6 minutes after the inlet. The third portion (0.10 molar equivalents) was added 19.1 minutes after the inlet, the fourth portion (0.10 molar equivalents) was added 26.2 minutes after the inlet, the fifth portion (0.08 molar equivalents) was added 35.7 minutes after the inlet and the sixth portion (0.32 molar equivalents) was added 43.3 minutes after the inlet. Please note that the total amount of hydrochloric acid now was 1.2 molar equivalents. The time at the outlet (from COBR to CSTR) was 52.8 minutes.

Differences from experiment 6 to experiment 7 are bolded below.

In the seventh experiment the first portion (0.45 molar equivalents) was added at the inlet. The slurry of seed crystals was added 2.8 minutes after the inlet. The second portion of hydrochloric acid (0.15 molar equivalents) was added 7.6 minutes after the inlet. The third portion (0.10 molar equivalents) was added 19.1 minutes after the inlet, the fourth portion (0.10 molar equivalents) was added 26.2 minutes after the inlet, the fifth portion (0.08 molar equivalents) was added 35.7 minutes after the inlet and the sixth portion (0.32 molar equivalents) was added 47.2 minutes after the inlet. Please note that the total amount of hydrochloric acid now was 1.2 molar equivalents. The time at the outlet (from COBR to CSTR) was 52.8 minutes.

Differences from experiment 7 to experiment 8 are bolded below.

In the eighth experiment the first portion (0.45 molar equivalents) was added at the inlet. The slurry of seed crystals (now 3.1 w/w % instead of 2.0 w/w %) was added 2.8 minutes after the inlet. The second portion of hydrochloric acid (0.15 molar equivalents) was added 7.6 minutes after the inlet. The third portion (0.10 molar equivalents) was added 19.1 minutes after the inlet, the fourth portion (0.10 molar equivalents) was added 26.2 minutes after the inlet, the fifth portion (0.08 molar equivalents) was added 35.7 minutes after the inlet and the sixth portion (0.32 molar equivalents) was added 47.2 minutes after the inlet. Please note that the total amount of hydrochloric acid now was 1.2 molar equivalents. The time at the outlet (from COBR to CSTR) was 52.8 minutes.

The scaling nearby the addition point of the sixth portion of hydrochloric acid decreased a bit as a consequence of increasing the time between the addition of the fifth and sixth portion of hydrochloric acid. The filtration behavior of the crystals obtained above was the same as in the previous experiment. Surprisingly, the liquid content prior to drying was now somewhat lower than for crystals from production. The crystals were therefore investigated by scanning electronic microscopy (SEM). It was seen that the crystals differed a bit in shape from those in production (see FIG. 1). The crystals from this experiment were easier to pre-dry (by blowing with nitrogen) than crystals from production. The salt content in the crystals was also low (≤0.2 w/w %).

FIG. 1 illustrates: SEM-photographs of crystals from crystallization in a plug-flow reactor by adding hydrochloric acid according to the invention (top) and from the current batch process (bottom). We found that the crystals on the top in FIG. 1 were easier to separate from mother liquor than the crystals on the bottom of FIG. 1. We also found that the rest moisture prior to drying was considerably lower for the crystals on the top. The top crystals were also easier to dry, which means less investment for achieving a defined drying capacity or higher capacity in the existing drying equipment.

The product quality of the crystals was the same as in the first "package". The filtration behavior was generally improved a bit and it was also even easier to dry the crystals. The scaling observed at some of the additions of hydrochloric acid in "package" 1 disappeared in many of the experiments in the "second package".

It will be understood by a person skilled in the art that the Examples have been performed on a laboratory scale and that the conditions used may be adapted when putting the invention into practice on an industrial scale. For example, fewer portions of acid may be used.

The invention claimed is:

1. A method of purifying 5-acetamido-N,N'-bis(2,3-dihydroxypropyl)-2,4,6-triiodoisophathalamide, comprising:
- (i) adding a portion of acid to a stream comprising crude 5-acetamido-N,N'-bis(2,3-dihydroxypropyl)-2,4,6-triiodoisophathalamide in a solvent;
- (ii) continuously crystallising 5-acetamido-N,N'-bis(2,3-dihydroxypropyl)-2,4,6-triiodoisophathalamide from the crude 5-acetamido-N,N'-bis(2,3-dihydroxypropyl)-2,4,6-triiodoisophathalamide, with removal of at least a fraction of the solvent, wherein the crystallisation is carried out in a continuous reactor, wherein the continuous reactor is a plug flow reactor;

wherein at least three further portions of acid are added to the continuous reactor during the crystallisation.

2. The method of claim 1, wherein the acid in step (i) is added to the stream comprising the crude 5-acetamido-N,N'-bis(2,3-dihydroxypropyl)-2,4,6-triiodoisophathalamide in an amount of 0.3-0.6 molar equivalents, 0.4-0.5 molar equivalents, or approximately 0.45 molar equivalents with respect to the crude 5-acetamido-N,N'-bis(2,3-dihydroxypropyl)-2,4,6-triiodoisophathalamide.

3. The method of claim 1, wherein the at least three portions of acid are each added to the continuous reactor in an amount of 0.05-0.6 molar equivalents with respect to crude 5-acetamido-N,N'-bis(2,3-dihydroxypropyl)-2,4,6-triiodoisophathalamide.

4. The method of claim 1, wherein each of the at least three portions of acid are added to the continuous reactor in an amount of between 0.1 and 0.5 molar equivalents with respect to the crude 5-acetamido-N,N'-bis(2,3-dihydroxypropyl)-2,4,6-triiodoisophathalamide.

5. The method of claim 1, wherein the at least three further portions of acid are at least five further portions of acid, wherein:
- (i) the first of the at least five portions of acid is added to the continuous reactor in an amount of 0.1-0.2 molar equivalents with respect to the crude 5-acetamido-N,N'-bis(2,3-dihydroxypropyl)-2,4,6-triiodoisophathalamide;
- (ii) the second of the at least five portions of acid is added to the continuous reactor in an amount of 0.5-1.5 molar equivalents with respect to the crude 5-acetamido-N,N'-bis(2,3-dihydroxypropyl)-2,4,6-triiodoisophathalamide;
- (iii) the third of the at least five portions of acid is added to the continuous reactor in an amount of 0.5-1.5 molar equivalents with respect to the crude 5-acetamido-N,N'-bis(2,3-dihydroxypropyl)-2,4,6-triiodoisophathalamide;
- (iv) the fourth of the at least five portions of acid is added to the continuous reactor in an amount of 0.03-0.11 molar equivalents with respect to the crude 5-acetamido-N,N'-bis(2,3-dihydroxypropyl)-2,4,6-triiodoisophathalamide; and
- (v) the fifth of the at least five portions of acid is added to the continuous reactor in an amount of 0.1-0.5 molar equivalents with respect to the crude 5-acetamido-N,N'-bis(2,3-dihydroxypropyl)-2,4,6-triiodoisophathalamide.

6. The method of claim 1, wherein the at least three further portions of acid are at least five further portions of acid, wherein:

(i) the first of the at least five portions of acid is added at a time between 9% and 19% of the total residence time; and/or (ii) the second of the at least five portions of acid is added at a time between 31% and 41% of the total residence time; and/or (iii) the third of the at least five portions of acid is added at a time between 44% and 54% of the total residence time; and/or (iv) the fourth of the at least five portions of acid is added at a time between 61% and 71% of the total residence time; and/or (v) the fifth of the at least five further portions of acid is added at a time between 84% and 94% of the total residence time.

7. The method of claim 1, wherein the total amount of acid added in steps (i) and (ii) of claim 1 is 1 to 1.2 molar equivalents with respect to the crude 5-acetamido-N,N'-bis (2,3-dihydroxypropyl)-2,4,6-triiodoisophathalamide.

8. The method of claim 1, wherein seed crystals are added to the continuous reactor.

9. The method of claim 5, wherein seed crystals of 5-acetamido-N,N'-bis(2,3-dihydroxypropyl)-2,4,6-triiodo-isophathalamide are added to the continuous reactor with or after the acid in step i) and before the at least five further portions of acid are added to the continuous reactor.

10. The method of claim 1, wherein the first portion of acid as recited in step (i) is added at the inlet of the continuous reactor where the stream enters; wherein the stream comprises crude 5-acetamido-N,N'-bis(2,3-dihydroxypropyl)-2,4,6-triiodoisophathalamide in a solvent.

11. The method of claim 1, wherein at least a fraction of the solvent is removed during the continuous crystallization of step (ii) to maintain supersaturation by: (i) distillation or (ii) azeotropic distillation.

12. The method of claim 1, wherein the crystallisation process is performed in one or more crystallisation units within the continuous reactor, and the crude 5-acetamido-N,N'-bis(2,3-dihydroxypropyl)-2,4,6-triiodoisophathalamide is fed into the crystallisation units at constant rates.

13. The method of claim 12, the process further comprising continuously withdrawing crystalline 5-acetamido-N,N'-bis(2,3-dihydroxypropyl)-2,4,6-triiodoisophathalamide from the crystallization units at a constant rate, wherein the volume load of the crystallization unit is kept constant.

14. The method of claim 1, wherein the acid is:

(i) a water-soluble inorganic acid; or (ii) selected from the group of sulphuric acid, nitric acid and hydrochloric acid; or (iii) hydrochloric acid.

* * * * *